(12) United States Patent
Young et al.

(10) Patent No.: US 11,998,489 B2
(45) Date of Patent: *Jun. 4, 2024

(54) GOGGLE SYSTEMS AND METHODS

(71) Applicant: 100% SPEEDLAB, LLC, San Diego, CA (US)

(72) Inventors: Michael D. Young, San Diego, CA (US); Dennis C. Tan, San Diego, CA (US); Ludovic Francis Boinnard, San Diego, CA (US)

(73) Assignee: 100% Speedlab, LLC, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/818,696

(22) Filed: Aug. 9, 2022

(65) Prior Publication Data

US 2023/0072304 A1 Mar. 9, 2023

Related U.S. Application Data

(63) Continuation of application No. 16/532,362, filed on Aug. 5, 2019, now Pat. No. 11,406,538, which is a continuation of application No. PCT/US2019/020428, filed on Mar. 1, 2019.

(60) Provisional application No. 62/772,575, filed on Nov. 28, 2018, provisional application No. 62/638,026, filed on Mar. 2, 2018, provisional application No. 62/638,011, filed on Mar. 2, 2018.

(51) Int. Cl.
*A61F 9/02* (2006.01)

(52) U.S. Cl.
CPC .............. *A61F 9/025* (2013.01); *A61F 9/026* (2013.01); *A61F 9/028* (2013.01); *A61F 9/029* (2013.01)

(58) Field of Classification Search
CPC .......... A61F 9/025; A61F 9/026; A61F 9/028; A61F 9/029
See application file for complete search history.

(56) References Cited

U.S. PATENT DOCUMENTS

| | | | | |
|---|---|---|---|---|
| 2,430,881 | A * | 11/1947 | Lehmberg | A61F 9/023 2/437 |
| 8,356,895 | B2 * | 1/2013 | Jackson | A61F 9/023 351/159.01 |
| 11,406,538 | B2 * | 8/2022 | Young | A61F 9/028 |

* cited by examiner

*Primary Examiner* — Katherine M Moran
(74) *Attorney, Agent, or Firm* — Kolitch Romano Dascenzo Gates LLC

(57) ABSTRACT

Goggles and eyewear with various features may be described herein. Such goggles and eyewear may include lenses that allow for the installation of larger roll-off films, adjustable nose sections to increase comfort of a wearer, sweat management systems that include a permeable gasket and a gutter, lens attachment systems, and co-molded frames of multiple different materials.

19 Claims, 14 Drawing Sheets

GOGGLE SYSTEMS AND METHODS

CROSS-REFERENCE TO RELATED APPLICATIONS

This application is a continuation of U.S. patent application Ser. No. 16/532,362, now U.S. Pat. No. 11,406,538. The following applications and materials are incorporated herein, in their entireties, for all purposes: U.S. patent application Ser. No. 16/698,274, filed Nov. 27, 2019; U.S. patent application Ser. No. 16/532,362, filed Aug. 5, 2019; International Patent Application No. PCT/US2019/020428, filed Mar. 1, 2019; U.S. Provisional Patent Application No. 62/772,575, filed Nov. 28, 2018; U.S. Provisional Patent Application No. 62/638,026, filed Mar. 2, 2018; and U.S. Provisional Patent Application No. 62/638,011, filed Mar. 2, 2018. However, such material is only incorporated to the extent that no conflict exists between the incorporated material and the statements and drawings set forth herein. In the event of any such conflict, including any conflict in terminology, the present disclosure is controlling.

TECHNICAL FIELD

One or more embodiments relate generally to eyewear including goggles and glasses systems and, more particularly, to sport goggles and sport glasses with features to improve user comfort and functionality.

BACKGROUND

Sport goggles or glasses may be worn by a wearer for various sports or activities, such as motorsports, powersports, snowsports, watersports, biking, or the like, to protect the eyes of the wearer. Sport goggles or glasses may be worn over an upper portion of the wearer's face, such as over the cheekbones, nose, forehead, and/or other portions of the wearer's face. The perimeter of the sport goggle may include seals and/or gaskets that conform to a user's face. As the seals and/or gaskets of the sports goggles contact the user's face, such seals and/or gaskets may have a great effect on user comfort.

Furthermore, the sport goggle may be installed with a roll-off film system to preserve a field of view on the lens of the sport goggle. In particular, the roll-off film system may stretch a section of a clear film across the lens of the sport goggle. When the section of the clear film is covered with dirt or debris from the activity, the roll-off film system may convey the used section of the clear film off the lens and a new section of the film may be conveyed onto the lens to provide a clear field of view for the user. As such, the larger amount of lens area that the roll-off film covers, the greater the effectiveness of the roll-off film.

SUMMARY

Systems and methods are provided in accordance with one or more embodiments of sports goggles and glasses. The sports goggles and glasses described herein may include a variety of features that improve user comfort, manufacturability, and performance.

In an embodiment, an eyewear frame including a first frame surface, a second frame surface including a perforation, where the second frame surface is configured to be disposed closer to a user's face than the first frame surface when the eyewear frame is worn by a user and where the perforation is configured to pass moisture from an one side of the second frame surface to an other side of the second frame surface, and a connecting surface connected to the first frame surface and the second frame surface to define a channel and configured to receive moisture passed through the perforation may be provided.

In certain embodiments, a gasket coupled to the second frame surface and configured to conform to a portion of the user's face and configured to pass the moisture from the user's face to the second frame surface may be further provided. In certain such embodiments, the gasket includes a moisture permeable first gasket portion and a moisture impermeable second gasket portion. In certain such embodiments, the eyewear frame defines an interior portion and wherein the second gasket portion is disposed closer to the interior portion than the first gasket portion.

In certain embodiments, the eyewear frame defines an interior portion and the connecting surface defines at least a portion of a perimeter of the interior portion. In certain such embodiments, the interior portion includes a top portion, a left portion, a right portion, and a bottom portion, and the connecting surface defines at least the top portion and parts of the left portion and the right portion. In certain embodiments, the eyewear frame further includes a lens vent configured to be disposed farther from the user's face than the first frame surface when the eyewear frame is worn by the user.

In certain embodiments, a moisture exit configured to receive moisture from the connecting surface may be further provided.

In another embodiment, eyewear that includes an eyewear frame and a lens retainer coupled to the eyewear, the lens retainer may include a first retainer end coupled to a first portion of the eyewear frame and a second retainer end coupled to a second portion of the eyewear frame, where the lens retainer is configured to move between a first position and a second position, where the second retainer end does not contact the eyewear frame in the first position, and where the second retainer end is coupled to the eyewear frame in the second position may be provided.

In certain embodiments, the eyewear frame includes an opening and the second retainer end includes a snap configured to hold the second retainer end to the eyewear frame when the snap is engaged with the opening.

In certain embodiments, the first retainer end includes a hinge configured to rotate the lens retainer relative to the eyewear frame.

In certain embodiments, the lens retainer is molded with the eyewear frame and the lens retainer is configured to flex relative to the eyewear frame.

In certain embodiments, the eyewear may further include a lens coupled to the eyewear frame, where the lens retainer is configured to hold the lens relative to the eyewear frame in the second position. In certain such embodiments, the eyewear frame includes an engagement pocket and the lens includes a front surface, a back surface, and a protrusion configured to be inserted into the engagement pocket to hold the lens relative to the eyewear frame. In certain such embodiments, the eyewear frame includes a plurality of engagement pockets and the lens includes a plurality of protrusions, each protrusion configured to be inserted into a respective engagement pocket, where at least one of the protrusions is disposed on the front surface and where at least another of the protrusions is disposed on the back surface.

In a further embodiment, an eyewear frame including a first frame portion that may include a first frame side, a second frame side and an opening, where the second frame side is configured to be disposed closer to a user's face than the first frame side when the eyewear frame is worn by a user, and where the first frame portion comprises a first material, and a second frame portion that may extend from the first frame side to the second frame side via the opening, where the second frame portion includes a second material with a modulus of elasticity lower than the first material may be provided.

In certain embodiments, a lens coupled to the eyewear frame and configured to contact the second frame portion to deform the second frame portion may be further provided In certain embodiments, the second frame portion is co-molded with the first frame portion.

In certain embodiments, a method of manufacturing may be provided, the method including molding, in a first tool, the first material to form the eyewear frame and molding, in the first tool, the second material to form the second frame portion. In certain such embodiments, molding the first material is performed during a first timeframe, molding the second material is performed during a second timeframe, and the first timeframe and the second timeframe at least partially overlap.

A more complete understanding of embodiments of the invention will be afforded to those skilled in the art, as well as a realization of additional advantages thereof, by a consideration of the following detailed description of one or more embodiments. Reference will be made to the appended sheets of drawings that will first be described briefly.

BRIEF DESCRIPTION OF THE DRAWINGS

Embodiments of the invention and their advantages are best understood by referring to the detailed description that follows. It should be appreciated that like reference numerals are used to identify like elements illustrated in one or more of the Figures.

DETAILED DESCRIPTION

Sports goggles and other eyewear are described herein. For the purposes of this disclosure, features and techniques of goggles and/or sports goggles described herein may also be used on other eyewear, such as glasses, sunglasses, and/or other wearable items. Accordingly, "goggle" or "sports goggle" may also generically refer to such other eyewear.

In various embodiments, a goggle frame including a nose section configured to be disposed proximate a user's nose, where the nose section comprises a plurality of flexible fingers, and where each flexible finger is configured to be adjusted independent of the other flexible fingers may be described herein. In another embodiment, a goggle lens including a front surface, a back surface, and a protrusion disposed on the front surface and configured to contact a nose section of a goggle frame to space the nose section of the goggle frame away from the front surface may be described herein. The goggle frame and the goggle lens may be coupled together to form a goggle.

In other embodiments, an eyewear frame including a first frame surface, a second frame surface, and a connecting surface may be described herein. The second frame surface may include a perforation and the connecting surface may be connected to the first frame surface and the second frame surface to define a channel and configured to receive moisture passed through the perforation. The second frame surface may be configured to be disposed closer to a wearer's face than the first frame surface when the eyewear frame is worn by the wearer and the perforation may be configured to pass moisture from one side of the second frame surface to another side of the second frame surface. In another embodiment, eyewear that includes an eyewear frame and a lens retainer may be described herein. The lens retainer may be coupled to the eyewear and may include a first retainer end coupled to a first portion of the eyewear frame and a second retainer end coupled to a second portion of the eyewear frame. The lens retainer may be configured to move between a first position and a second position, where the second retainer end does not contact the eyewear frame in the first position, and where the second retainer end is coupled to the eyewear frame in the second position. In a further embodiment, an eyewear frame that includes a first frame portion and a second frame portion may be described herein. The first frame portion may include a first frame side, a second frame side and an opening, where the second frame side is configured to be disposed closer to a user's face than the first frame side when the eyewear frame is worn by a user, and where the first frame portion comprises a first material. The second frame portion may extend from the first frame side to the second frame side via the opening, where the second frame portion includes a second material with a modulus of elasticity lower than the first material.

Figure 1:
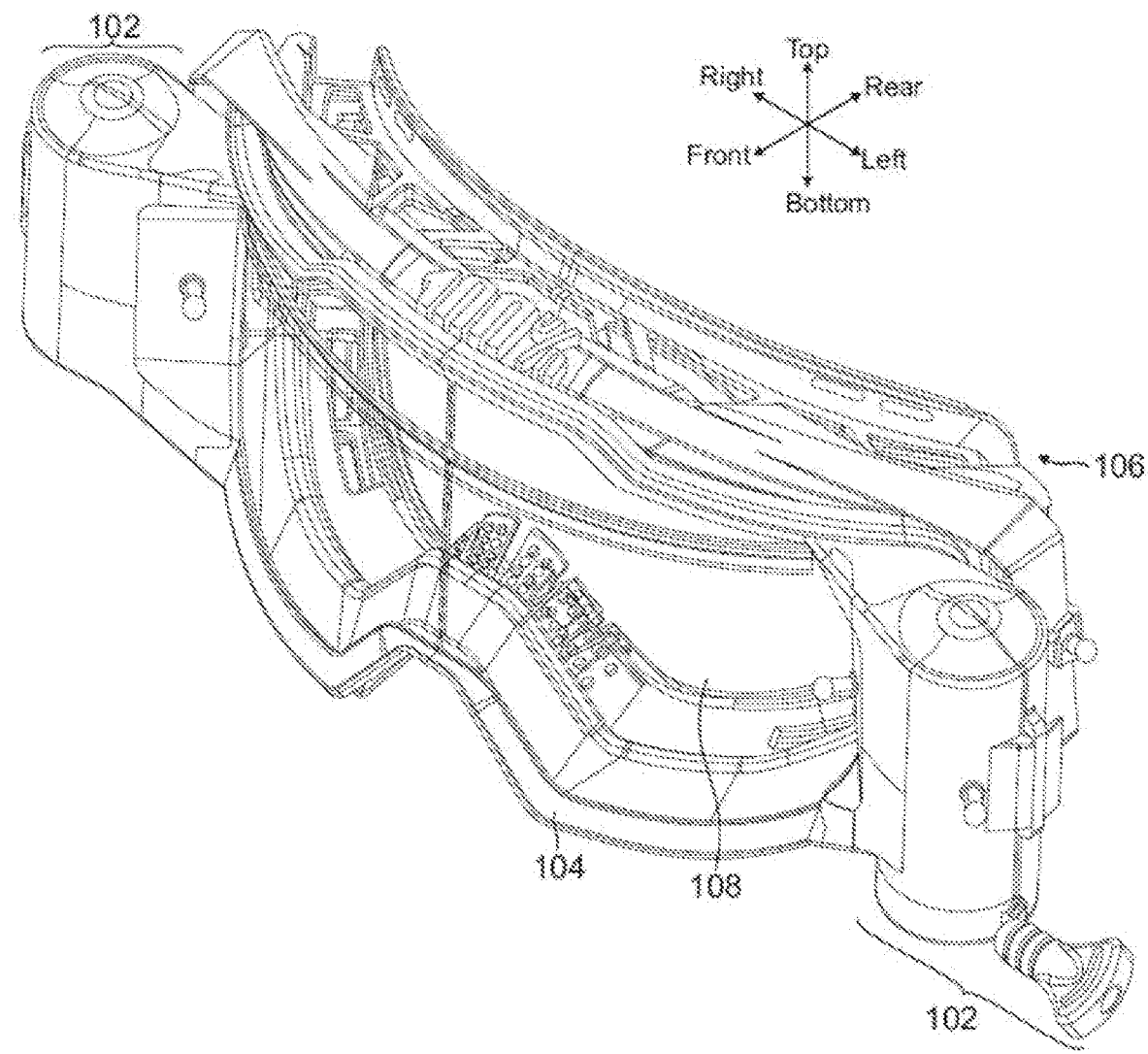
FIG. 1 shows a perspective front view of a roll-off film system installed on a goggle, in accordance with an embodiment.

FIG. 1 shows a perspective front view of a roll-off film system installed on a goggle, in accordance with an embodiment. As shown in FIG. 1, a goggle frame 106 may be installed with a roll-off film system 102. In particular, the roll-off film system 102 may be installed to the goggle frame 106 via an adaptor 104. The adaptor 104 may adapt the goggle frame 106 to use different goggle lenses and/or accessories. For example, the adaptor 104 may adapt the goggle frame 106 to use lenses of different sizes, shapes, curvatures, and the like. The adaptor 104 also may adapt the goggle frame 106 to use roll-off film systems of different film sizes.

The roll-off film system 102 may be attached to the lens 108, which is installed in the adaptor 104. The adaptor 104 may be attached to the goggle frame 106. In some embodiments, the lens 108 may be installed directly to the goggle frame 106, without the adaptor 104. Thus, the roll-off film system 102 may be installed on the goggle frame 106 without using the adaptor 104. The roll-off film system 102 may stretch a section of a film on the lens 108. When the section of the film becomes filled with dirt or debris, the used section of the film may be conveyed off the lens 108 and a new section of the film may replace the used section of the film to provide the user with clear field of view on the lens 108.

Figure 2:
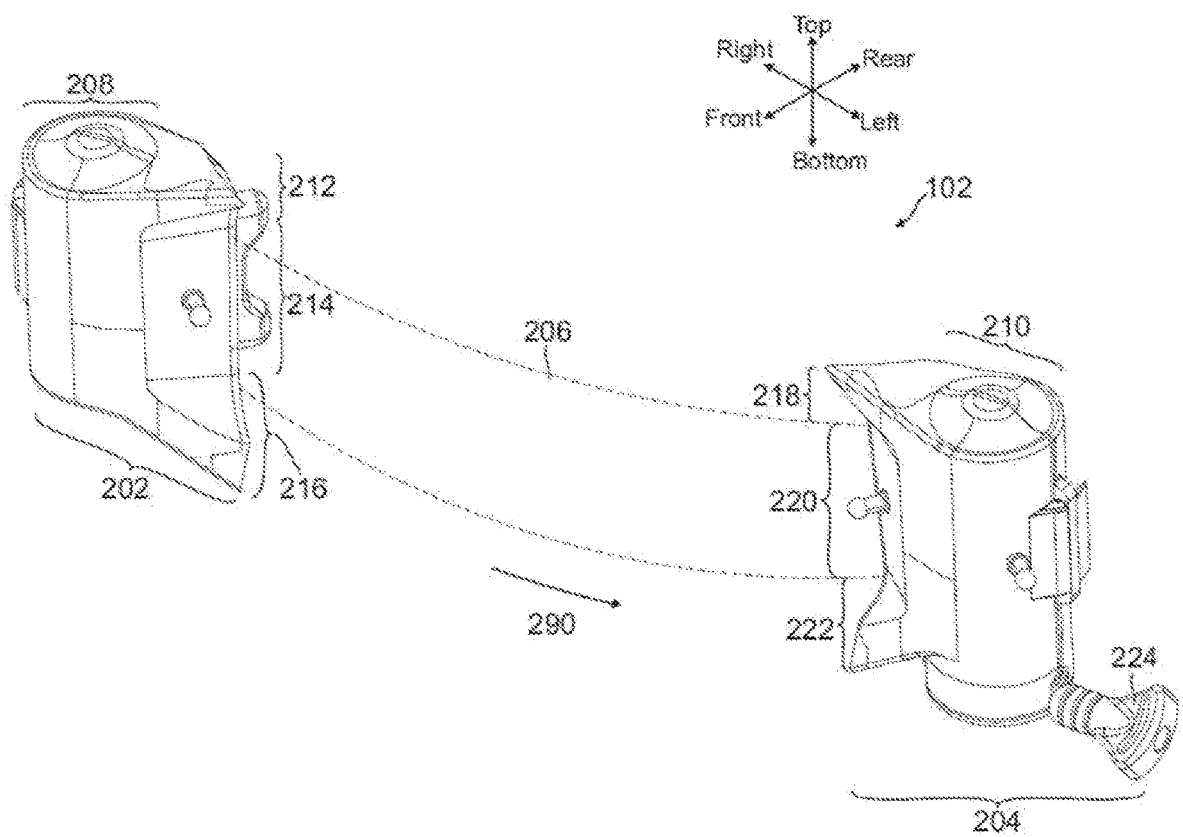
FIG. 2 shows a perspective front view of the roll-off film system of FIG. 1, in accordance with an embodiment.

FIG. 2 shows a perspective front view of the roll-off film system of FIG. 1, in accordance with an embodiment. As shown in FIG. 2, the roll-off film system 102 may include a film dispensing canister 202 and a film receiving canister 204. The film dispensing canister 202 may dispense a section of a film 206 across the lens 108 (shown in FIG. 1) toward the film receiving canister 204. The film receiving canister 204 may receive the film 206 from the film dispensing canister 202. The film receiving canister 204 may include a pull cord handle 224, which is attached to an end of a string configured to drive a conveyance of the film 206 from the film dispensing canister 202 to the film receiving canister 204 in a film conveying direction 290. For example, when the section of the film 206 resting on the lens 108 becomes filled with dirt or debris, a user may pull the pull cord handle 224 to roll the used section of the film 206 into the film receiving canister 204 and to convey a new section of the film 206 onto the lens 108 to provide a clear field of view on the lens 108.

The film dispensing canister 202 may include a film storage portion 208 within which the film 206 may be stored. The film dispensing canister 202 also may include an upper wing portion 212, a lower wing portion 216, and a blade portion 214 disposed between the upper wing portion 212 and the lower wing portion 216. The upper wing portion 212 and the lower wing portion 216 may protrude further downstream in the film conveying direction 290 than the blade portion 214. The film 206 may exit the film dispensing canister 202 through an opening at the blade portion 214.

The film receiving canister 204 may include a film storage portion 210 within which the film 206 received from the film dispensing canister 202 may be stored. The film receiving canister 204 also may include an upper wing portion 218, a lower wing portion 222 and, a blade portion 220 disposed between the upper wing portion 218 and the lower wing portion 222. The upper wing portion 218 and the lower wing portion 222 may protrude further upstream in the film conveying direction 290 than the blade portion 220. The film 206 may be conveyed into the film receiving canister 204 through an opening at the blade portion 220. Furthermore, the film dispensing canister 202 may also include a lens attachment mechanism configured to attach the film dispensing canister 202 to the lens 108. Similarly, the film receiving canister 204 may also include a lens attachment mechanism configured to attach the film receiving canister 204 to the lens 108.

Figure 3:
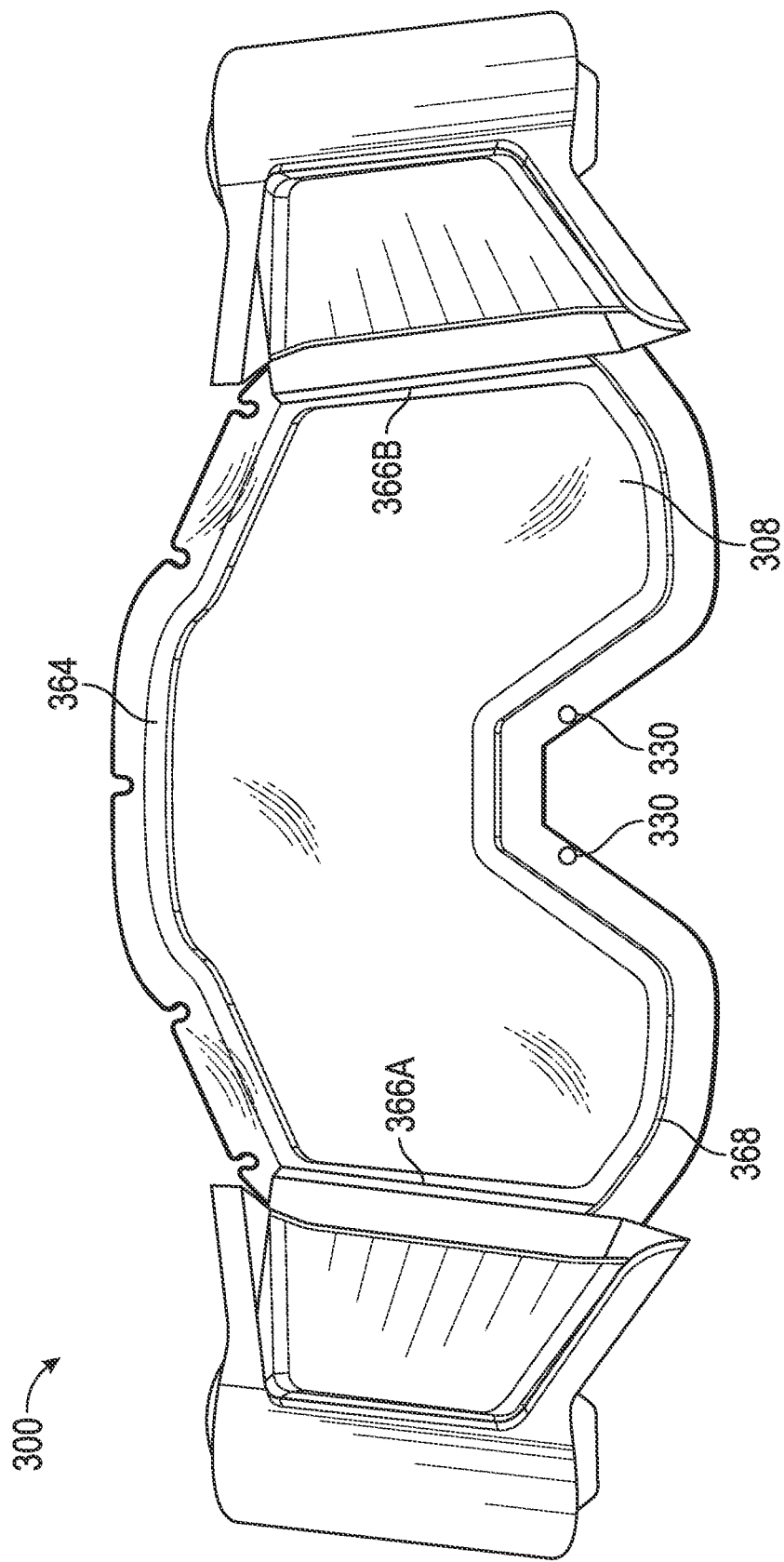
FIG. 3 shows a front view of a goggle lens, in accordance with an embodiment.

FIG. 3 shows a front view of a goggle lens, in accordance with an embodiment. Goggle lens assembly 300 of FIG. 3 includes lens 308 that includes protrusions 330. Lens 308 may be a clear and/or tinted lens that allows a wearer to see through lens 308. Lens 308 may include a front surface and a back surface. When a goggle is worn by a wearer, the front surface of lens 308 may be an outside surface of the lens and the back surface of lens 308 may face the user's face.

Protrusions 330 may be disposed on a portion of lens 308 (e.g., a portion of lens 308 near a nose portion that includes a cutout for a wearer's nose and/or at other portions of lens 308 such as along the periphery of lens 308) and may be configured to be disposed under a portion of goggle frame 106 (e.g., under a bezel of goggle frame 106) to space and/or raise a portion of goggle frame 106 clear of lens 308 to allow for film to pass underneath that portion of goggle frame 106. Thus, protrusions 330 may space and/or raise goggle frame 106 to allow for a larger version of film 206 to be installed on and dispensed across lens 108. In certain embodiments, protrusions 330 may be disposed on the front surface of lens 308 as film 206 is also disposed on the front surface of lens 308.

FIG. 3 also illustrates top portion 364, right portion 366A, left portion 366B, and bottom portion 368. Such portions may correspond to the general orientation of the goggle and/or goggle lens when the goggle is worn. As such, top portion 364 may be a top facing portion that may be located near a wearer's brow when worn. Right and left portions 366A and 366B may be located to the right and left, respectively, of a wearer's eyes when the goggle is worn. Bottom portion 368 may be a bottom facing portion that may be located near a wearer's nose, lip, or cheeks when worn. Though top portion 364, right portion 366A, left portion 366B, and bottom portion 368 are shown in FIG. 3, such orientations may also be used to describe portions of goggles (e.g., goggle frame) and other eyewear described herein.

Figure 4:
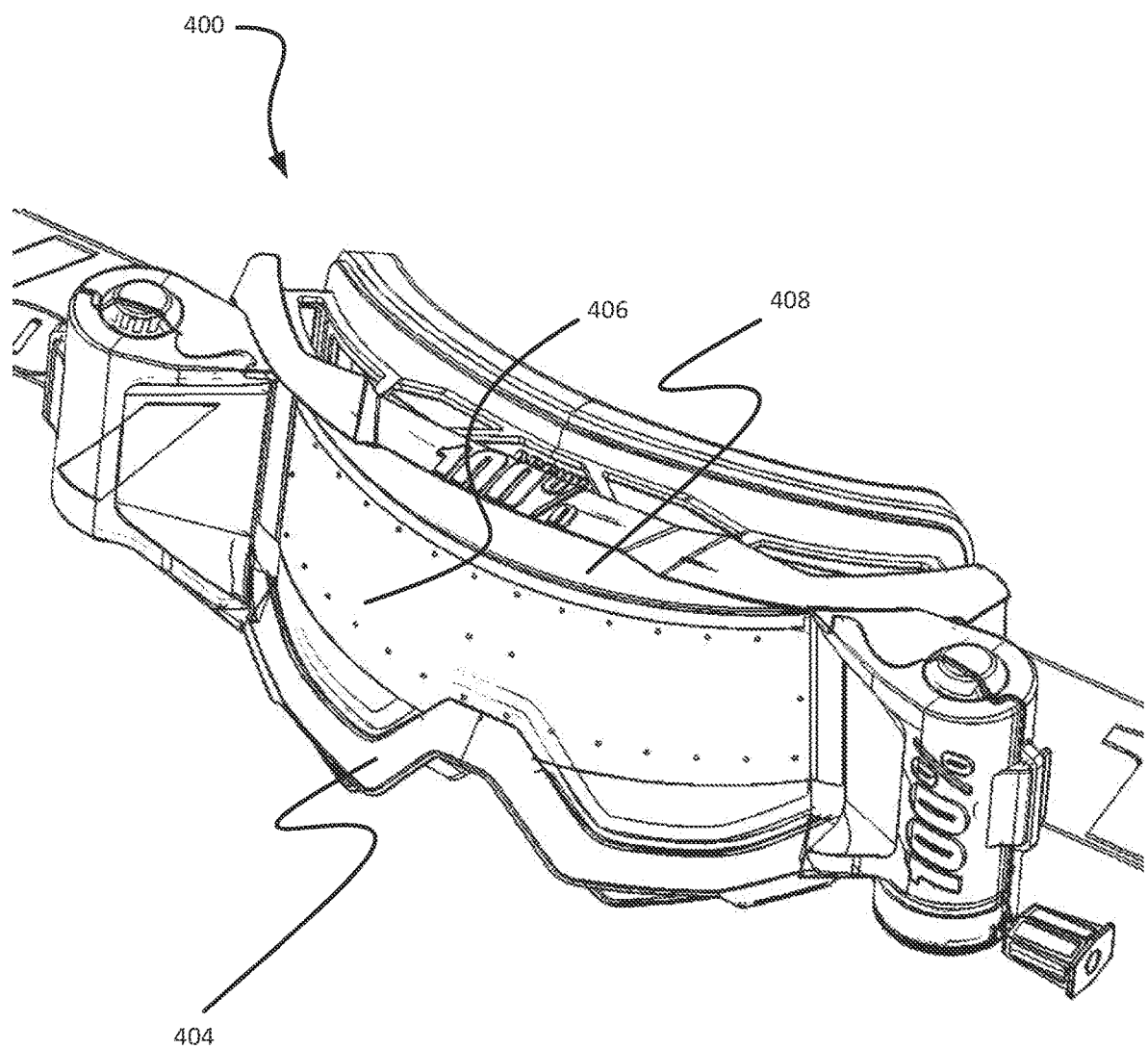
FIG. 4 shows a perspective front view of the goggle lens of FIG. 3 and associated roll-off film system installed on a goggle, in accordance with an embodiment.

FIG. 4 shows a perspective front view of the goggle lens of FIG. 3 and associated roll-off film system installed on a goggle, in accordance with an embodiment. FIG. 4 shows goggle 400 with goggle frame 404, lens 408, and film 406.

Goggle frame 404 may include multiple components. For example, the back surface of lens 408 may be disposed on a back goggle frame while the front surface of lens 408 may be disposed against a front goggle frame or bezel. The back goggle frame and front goggle frame or bezel may couple together to hold lens 408 within goggle frame 404. Other embodiments of goggle frame 404 may include a one piece goggle frame that includes a groove within goggle frame 404 for lens 408 to be inserted within. The groove may hold lens 408.

Lens 408 may include protrusions configured to be disposed underneath the back goggle frame, front goggle frame, and/or bezel when lens 408 is coupled to goggle frame 404 and/or space the groove that lens 408 is inserted into. Such protrusions may space and/or raise at least a portion of the corresponding back goggle frame, front goggle frame, and/or bezel (e.g., the portion near the nose section of the goggle frame 404, the nose section being the portion of the goggle frame 404 configured to accommodate a wearer's nose) and/or space the groove so that there is a gap between lens 408 and corresponding portion of goggle frame 404. The gap may allow for film 406 to pass underneath the portion of the corresponding back goggle frame, front goggle frame, bezel, and/or groove. Thus, the protrusions may allow for a larger film 406 to be used and dispensed across lens 408, leading to improved wearer visibility.

Figure 5:
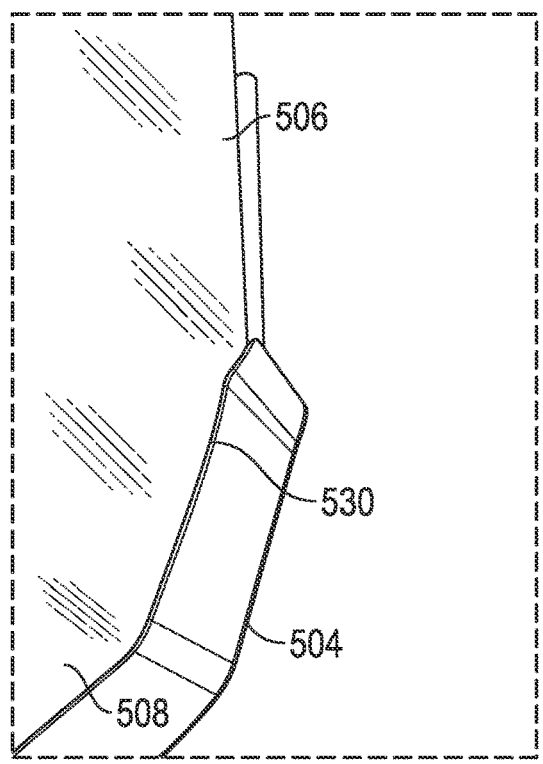
FIG. 5 shows a side view of the goggle lens of FIG. 3 and associated roll-off film system installed on a goggle, in accordance with an embodiment.

FIG. 5 shows a side view of the goggle lens of FIG. 3 and associated roll-off film system installed on a goggle, in accordance with an embodiment. FIG. 5 may further illustrate protrusion 530 that space and/or raise a portion of goggle frame 504 from lens 508 to create a gap. As shown in FIG. 5, protrusion 530 may space and/or raise goggle frame 504 near a nose portion of the goggle. Film 506 may pass under the spaced and/or raised portion of goggle frame 504.

Figure 6:
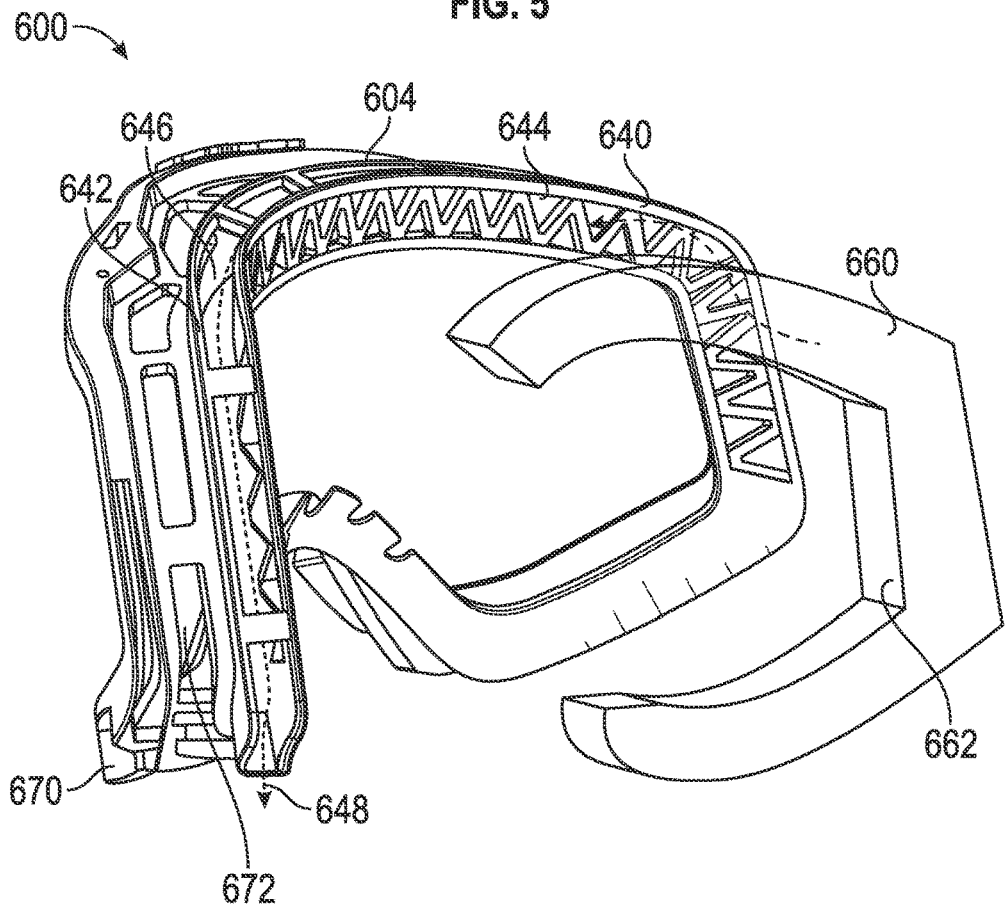
FIG. 6 shows a perspective view of a goggle frame and liner, in accordance with an embodiment.

FIG. 6 shows a perspective view of a goggle frame and liner, in accordance with an embodiment. Goggle 600 includes goggle frame 604 and gasket 660. Gasket 660 may be configured to conform to a wearer's face to increase wearer comfort. Thus, gasket 660 may be made from a deformable material. Additionally, at least a portion of gasket 660 may be a permeable material that allows for liquid to pass through that portion of gasket 660.

Goggle frame 604 may include a first frame surface 642, a second frame surface 640, and a connecting surface 646. First frame surface 642, second frame surface 640, and connecting surface 646 may define various surfaces of gutter 648. In certain other embodiments, gutter 648 may be further defined by other surfaces to provide an enclosed gutter, but as shown in FIG. 6, gutter 648 may be an open gutter. Gutter 648 may be configured to receive moisture (e.g., sweat of a wearer) through perforations 644 and direct the moisture away from the wearer's eyes. Gutter 648 may include a moisture exit configured to receive moisture that flows through gutter 648 (e.g., on connecting surface 646) and allow for moisture to exit gutter 648 and flow away from goggle frame 604.

Perforations 644 may be perforations within second frame surface 640. Second frame surface 640 may be a surface or portion of goggle frame 640 disposed closer to a wearer's face (e.g., closer than first frame surface 642). Second frame surface 640 may be coupled to gasket 660 on one side. At least some of the permeable portion of gasket 660 may be coupled to perforations 644 and thus moisture may be allowed to pass through the permeable portion of gasket 660 through perforations 644 into gutter 648. For example, sweat of a wearer may, instead of rolling down the wearer's brow into the user's eye, pass through the permeable portion of gasket 660 through perforations 644 of second frame surface 640 into gutter 648. Thus, the sweat may be directed away from the wearer and may increase wearer comfort.

Furthermore, gasket 660 may also include an impermeable portion 662. The impermeable portion 662 may be an interior portion of gasket 660 and may be configured to prevent moisture passing through the permeable portion of gasket 660 from entering into an interior portion of goggle 600 (e.g., the portion of goggle 600 where the user's eyes are located within). The interior portion of goggle 600 may be defined by one or more of first frame surface 642, second frame surface 640, and connecting surface 646. Thus, for example, the interior portion may include one or more of a top portion, a right portion, a left portion, and a bottom portion and connecting surface 646 may define a perimeter of the interior portion that includes one or more of the top portion, right portion, left portion, and bottom portion. Furthermore, the impermeable portion 662 of gasket 660 may also be disposed around at least part of the interior portion. Thus, impermeable portion 662 may further prevent moisture from reaching the interior portion and thus the eyes of the wearer.

Goggle frame 604 may additionally include a lens portion 670 configured to receive a lens and lens vent 672. Lens vent 672 may, in certain embodiments, be disposed farther from the user's face than first frame surface 642, connecting surface 646, and/or second frame surface 640 when goggle 600 is worn. Lens vent 672 may provide for ventilation into the interior portion.

Figure 7:
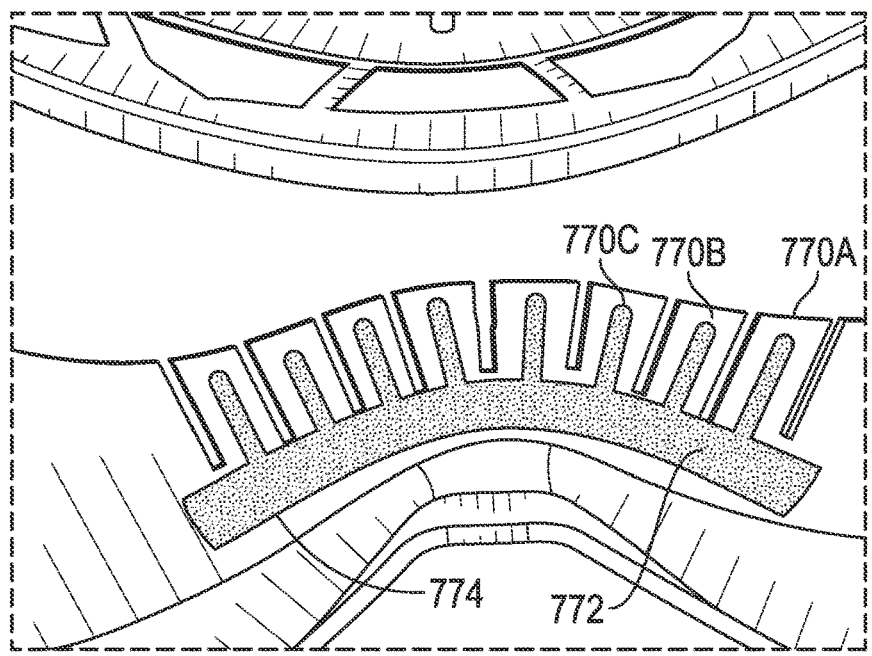
FIG. 7 shows a rear view of a nose section of a goggle frame, in accordance with an embodiment.

FIG. 7 shows a rear view of a nose section of a goggle frame, in accordance with an embodiment. FIG. 7 illustrates a goggle nose section 700 that includes deformable frame section 774 and flexible structure 772. Goggle nose section 700 may be a portion of the goggle that is configured to be disposed proximate a wearer's nose when worn.

In certain embodiments, goggle nose section 700 may be a part of a goggle or goggle frame. Typically, goggle nose section 700 may be covered by additional material (e.g., may be covered by a flexible covering such as liner material, rubber, plastic, or other such material that may be configured to contact a wearer) or may be exposed (e.g., the structure shown in FIG. 7 may not be covered by additional material).

Deformable frame section 774 may be a compliant section of the goggle frame. Deformable frame section 774 may, when the goggle is worn by the wearer, deform to cover a portion of a wearer's face. Deformable frame section 774 may be formed (e.g., manufactured) with a resting shape and may return to such a resting shape when the goggle is not worn by a wearer.

Flexible structure 772 may be coupled to deformable frame section 774. Flexible structure 772 may be an additional frame section formed separate from deformable frame section 774 and later coupled to deformable frame section 774 (e.g., via mechanical fasteners, adhesives, and/or via features of deformable frame section 774 and flexible structure 772) or may be produced with deformable frame section 774 (e.g., co-molded).

Flexible structure 772 may include flexible fingers 770A-C. In certain embodiments, flexible structure 772 may include any number of fingers. Each of flexible fingers 770A-C may be configured to be adjusted independent of the other flexible fingers. Each of flexible fingers 770A-C may be configured to allow a wearer to move the finger (e.g., through manual adjustment or through wearing the goggle and pushing the fingers into position through facial features of the wearer) into a position and to hold the position in the absence of force sufficient to move the fingers to another position. Each finger may thus be configured to hold a position until a threshold force has been exceeded. Once the threshold force has been exceeded, the fingers may be moved to another position.

Figure 8:
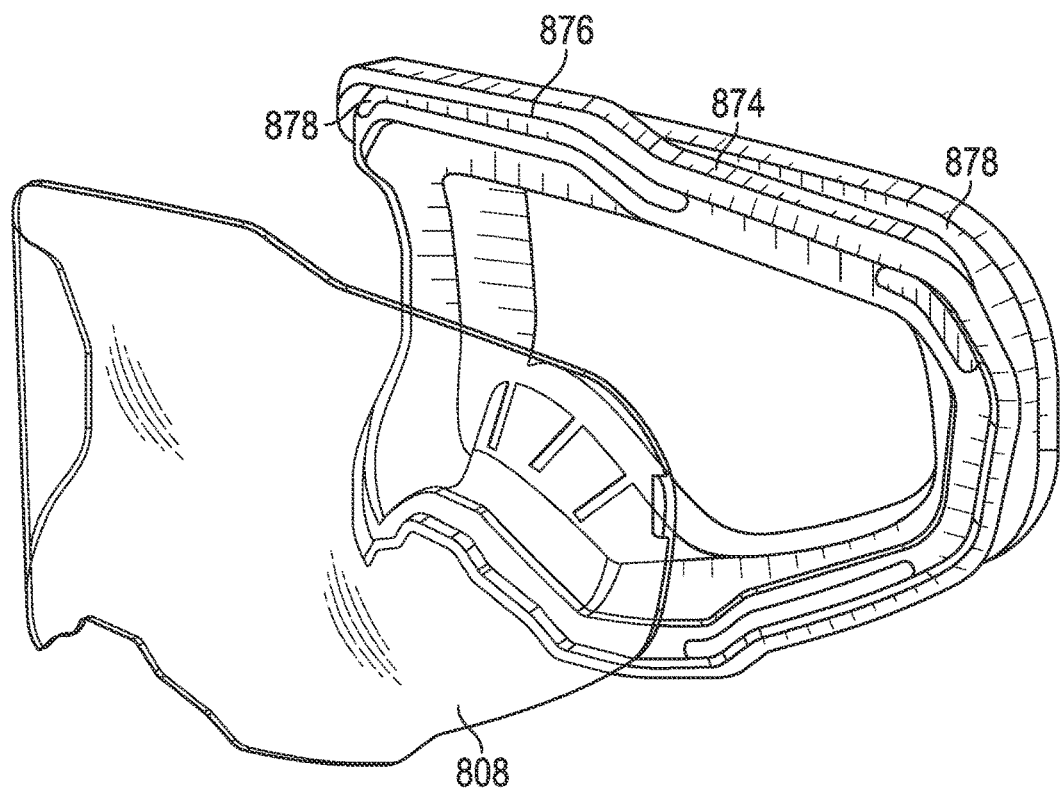
FIG. 8 shows a perspective front view of a goggle frame and lens, in accordance with an embodiment.

FIG. 8 shows a perspective front view of a goggle frame and lens, in accordance with an embodiment. Goggle 800 in FIG. 8 includes goggle lens 808, goggle frame first portion 874, and goggle frame second portion 878. Goggle lens 808 may be coupled to goggle frame first portion 874 and/or goggle frame second portion 878.

Goggle frame first portion 874 and goggle frame second portion 878 may be made from different materials. For example, goggle frame first portion 874 may be made from a first material and goggle frame second portion 878 may be made from a second material with a different modulus of elasticity. The first material may be stiffer (e.g., may have a higher modulus of elasticity) than the second material so that goggle frame first portion 874 can provide structural support to goggle 800. The second material may be a more flexible material that may conform to a wearer's face when goggle 800 is worn.

The more flexible goggle frame second portion 878 may also couple to goggle lens 808 to seal goggle lens 808 against the goggle frame when goggle lens 808 is coupled to the goggle frame. As such, goggle frame first portion 874 may include one or more slots 876 that allow goggle frame second portion 878 to extend from a first side to a second side (e.g., from a back side to a front side) of goggle frame first portion 874.

The goggle lens 808 may then contact at least a portion of goggle frame second portion 878 that is disposed on the second side when goggle lens 808 is coupled to the goggle frame. Goggle frame first portion 874 and/or goggle frame second portion 878 may include features configured to hold goggle lens 808, such as grooves, snaps, bolt and/or rivet holes, and/or other features that allow for goggle lens 808 to snapped or disposed into a certain area of goggle lens 808.

In certain embodiments, goggle frame first portion 874 and goggle frame second portion 878 may be produced jointly. That is, goggle frame first portion 874 and goggle frame second portion 878 may be co-molded. Thus, molding the of the goggle frame first portion 874 may be performed during a first timeframe and molding of the goggle frame second portion 878 may be performed during a second timeframe. The first timeframe and the second timeframe may at least partially overlap. Co-molding goggle frame first portion 874 and goggle frame second portion 878 may allow for simplified manufacturing while retaining frame portions made from different materials.

Figure 9:
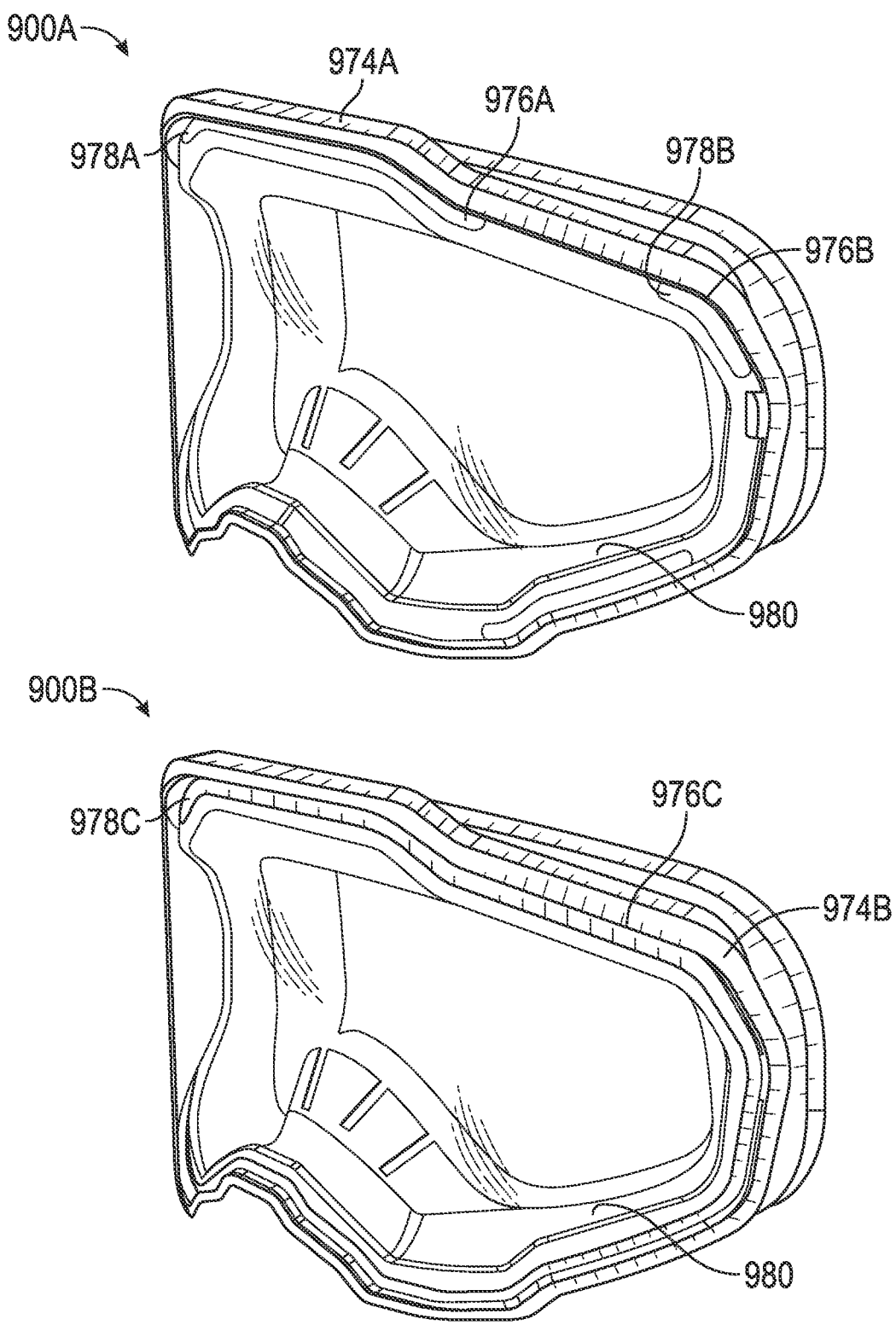
FIG. 9 shows perspective front views of other goggle frames and lenses, in accordance with further embodiments.

FIG. 9 shows perspective front views of other goggle frames and lenses, in accordance with further embodiments. FIG. 9 shows two configurations of goggles, goggles 900A and 900B respectively. Goggle 900A may include a plurality of slots 976A and 976B on goggle frame first portion 974A that each allow for goggle frame second portion (illustrated as goggle frame second portions 978A and 978B, but molded as the same structure) to pass from the first side to the second side. Goggle 900A may also include additional slots and such slots may be disposed around a perimeter of lens opening 980 of the goggle frame to form a gasket and seal lens opening 980 when goggle lens 808 is coupled to the goggle frame.

Goggle frame first portion 974B of goggle 900B includes a continuous slot 976C that may extend along the entire periphery of lens opening 980. Goggle frame second portion 978C may pass through slot 976C to form a gasket and seal lens opening 980.

Figure 10:
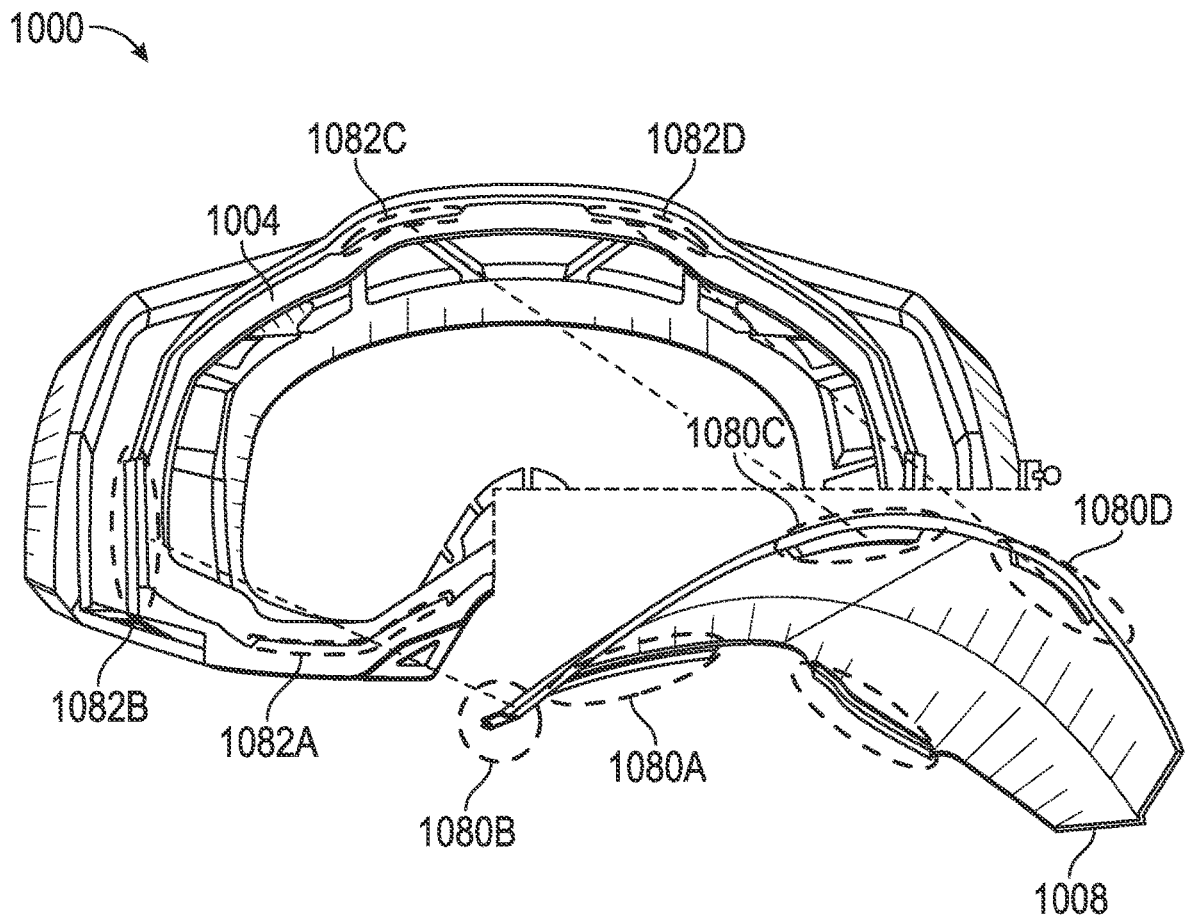
FIG. 10 shows a view of a goggle frame and lens, in accordance with an embodiment.

FIG. 10 shows a view of a goggle frame and lens, in accordance with an embodiment. FIG. 10 illustrates goggle 1000 that includes goggle frame 1004 and goggle lens 1008. Goggle frame 1004 includes engagement pockets 1082A-D and goggle lens 1008 includes protrusions 1080A-D. Protrusions 1080A-D may be located on goggle lens 1008 to correspond to the location of engagement pockets 1082A-D on goggle frame 1004. Thus, protrusions 1080A-D may be inserted into engagement pockets 1082A-D to hold goggle lens 1008 relative to goggle frame 1004.

Protrusions and engagement pockets may be disposed on one or more of the top portion, right portion, left portion, and bottom portion of the goggle lens 1008 and goggle frame 1004, respectively. In certain embodiments, protrusions and engagement pockets may be disposed on at least two of the portions to securely hold goggle lens 1008 relative to goggle frame 1004. Thus, the features of FIG. 10 may allow for goggle lens 1008 to snap into goggle frame 1004 and be held relative to goggle frame 1004.

In various embodiments, protrusions may be disposed on the front surface and/or the back surface of goggle lens 1008. Protrusion 1080B may be disposed on the front surface of goggle lens 1008 and protrusions 1080A, 1080C, and 1080D may be disposed on the back surface of goggle lens 1008. Engagement pockets 1082A-D may be correspondingly formed on goggle frame 1004. Thus, for example, goggle frame 1004 may include a location configured to receive goggle lens 1008 (e.g., a flat area, a groove, or another feature within goggle frame 1004) and engagement pockets 1082A-D may be disposed around the location. Thus, engagement pocket 1082B, corresponding to protrusion 1080B, may be disposed forward of the location while engagement pockets 1082A, 1082C, and 1082D, corresponding to protrusions 1080A, 1080C, and 1080D, may be disposed rearward of the location.

Figure 11A:
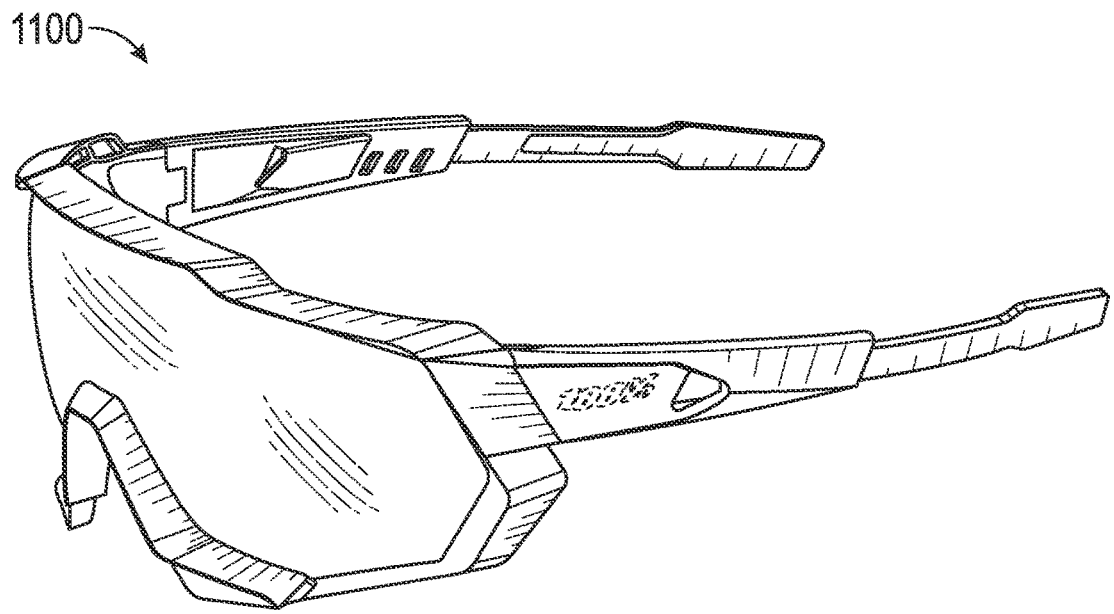
FIG. 11A shows a perspective side view of a sunglass, in accordance with an embodiment.

FIG. 11A shows a perspective side view of a sunglass, in accordance with an embodiment. FIG. 11A illustrates glasses 1100. Glasses 1100 may be a sunglass that incorporates one or more features described herein. For example, glasses 1100 may include the co-molded frame portions, permeable gaskets, perforations and gutters for moisture management, adjustable nose sections, and larger films described herein.

Figure 11B:
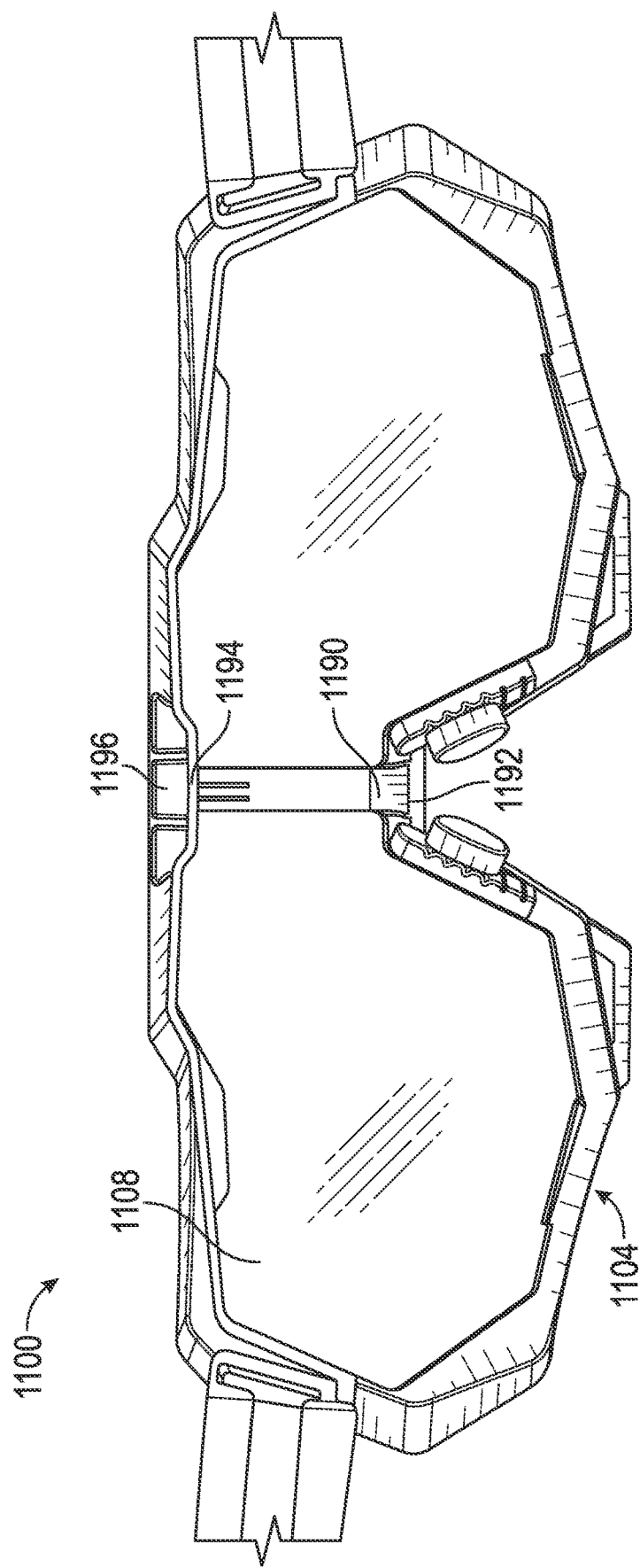
FIG. 11B shows a back view of the sunglass of FIG. 11A, in accordance with an embodiment.

FIG. 11B shows a back view of the sunglass of FIG. 11A, in accordance with an embodiment. Glasses 1100 includes frame 1104, lens 1108, and lens retainer 1190. Lens 1108 may be disposed within frame 1104 and lens retainer 1190 may be coupled to frame 1104 to hold lens 1108 to frame 1104.

Lens retainer 1190 may include a first retainer end 1192 and a second retainer end 1194. First retainer end 1192 may be coupled to frame 1104 (e.g., coupled in a hinged manner so that lens retainer 1190 may move relative to frame 1104). In certain embodiments, first retainer end 1192 may be coupled to frame 1104 through one or more hinges, bearings, mechanical fasteners (e.g., snaps, detents, posts), or other features. In other embodiments, first retainer end 1192 and lens retainer 1190 may be a part of frame 1104. That is, the lens retainer 1190 may be formed (e.g., molded) along with frame 1104 (or other component of glasses 1100, such as a feature of lens 1108) and may extend off a portion of frame 1104. In such an embodiment, lens retainer 1190 may be configured to be flexible to move between various positions and first retainer end 1192 may be where lens retainer 1190 meets frame 1104.

Lens retainer 1190 may be configured to move to a first position that creates an opening between lens retainer 1190 (e.g., the portion of lens retainer 1190 extending from first retainer end 1192) and frame 1004 for lens 1108 to be disposed within and/or coupled to frame 1104 (e.g., inserted into features of frame 1108). Thus, second retainer end 1194 does not contact frame 1104 when lens retainer 1190 is in the first position.

Lens retainer 1190 may also be configured to move to a second position to hold lens 1108 to frame 1104 (e.g., lock lens 1108 in place). In the second position, second retainer end 1194 may be coupled to, contact, or engage a feature 1196 of frame 1104. As such, second retainer end 1194 of lens retainer 1190 may include one or more features to hold second retainer end 1194 to or within feature 1196 of frame 1104. For example, second retainer end 1194 may include a snap, tab, embedded fastener, opening to receive a fastener, or other feature that can couple to or engage a portion of frame 1104 (e.g., feature 1196) to hold second retainer end 1194 to frame 1104 and be uncoupled and/or disengaged to allow for lens retainer 1190 to move to the first position. Frame 1104 may include corresponding features (e.g., an opening to receive a snap or tab or features to receive a fastener) at the portion of frame 1104 configured to couple to or engage second retainer end 1194.

As shown in FIG. 11B, first retainer end 1192 may be disposed on a bottom portion of frame 1104 and second retainer end 1194 may be disposed on a top portion of frame 1104. Other embodiments of lens retainer 1190 may dispose first retainer end 1192 and/or second retainer end 1194 at other locations on frame 1104. Furthermore, other embodiments may reverse the location of first retainer end 1192 and second retainer end 1194 from what is shown in FIG. 11B. Though lens retainer 1190 shown in FIG. 11B is described in context of glasses 1100, other embodiments may include a lens retainer on a goggle or other eyewear, as described herein.

Figure 12:
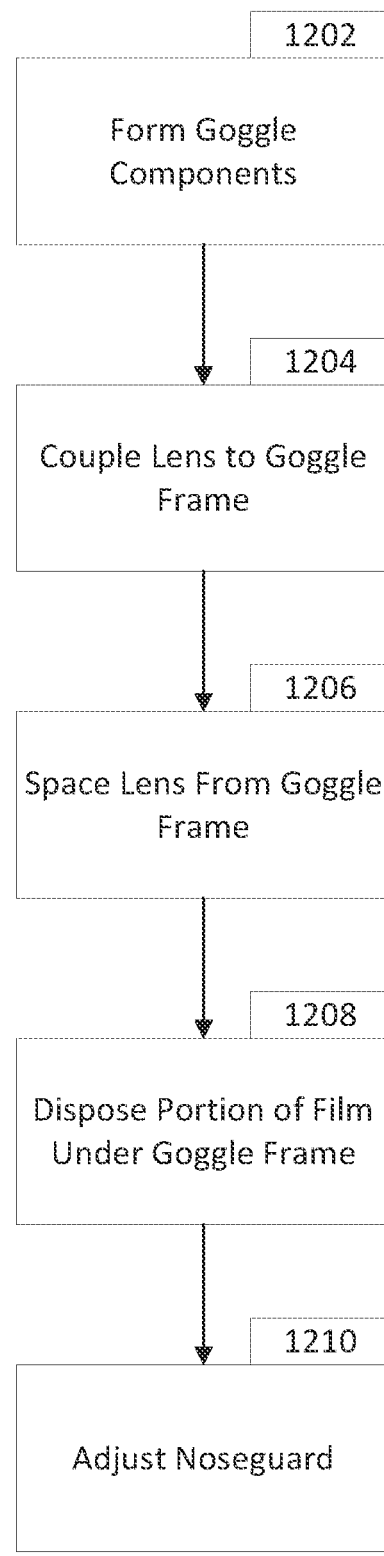
FIG. 12 shows a flowchart detailing a process for manufacturing and using a goggle, in accordance with an embodiment.

FIG. 12 shows a flowchart detailing a process for manufacturing and using a goggle, in accordance with an embodiment. In block 1202, various components of the goggle (e.g., lenses, frames, film, gaskets, and/or other components) are formed. Forming of the components may include, for example, forming a goggle frame that includes a plurality of frame portions that are co-molded together.

The lens is then coupled to the goggle frame in block 1204. One or more protrusions on the lens may be inserted into corresponding engagement pockets of the goggle frame. The lens may then be snapped into place and the engagement pockets may receive the protrusions to hold the goggle lens relative to the goggle frame. Furthermore, a gasket configured to conform to a wearer's face may be coupled to the goggle frame. The gasket may be a permeable gasket and may be placed over one or more perforations of the goggle frame to allow moisture to pass through the perforations and into a gutter of the goggle frame.

A portion of the goggle frame may be spaced and/or raised by one of more bump protrusions on the lens in 1206. A film dispenser may be coupled to the goggle in block 1208. Raising the goggle frame may create a gap and allow for film to pass under the portion of the goggle frame.

A wearer may adjust the noseguard in block 1210. The noseguard may include a nose section that includes an adjustable frame. The nose section may be adjusted to a position accepted to the wearer and the adjustable frame may then hold the position. The adjusted nose section may be a position that is comfortable to the user and the adjustable frame may hold the position to prevent any unwanted pressure on the portion of the wearer's face around the nose causing discomfort to the wearer.

Figure 13A:
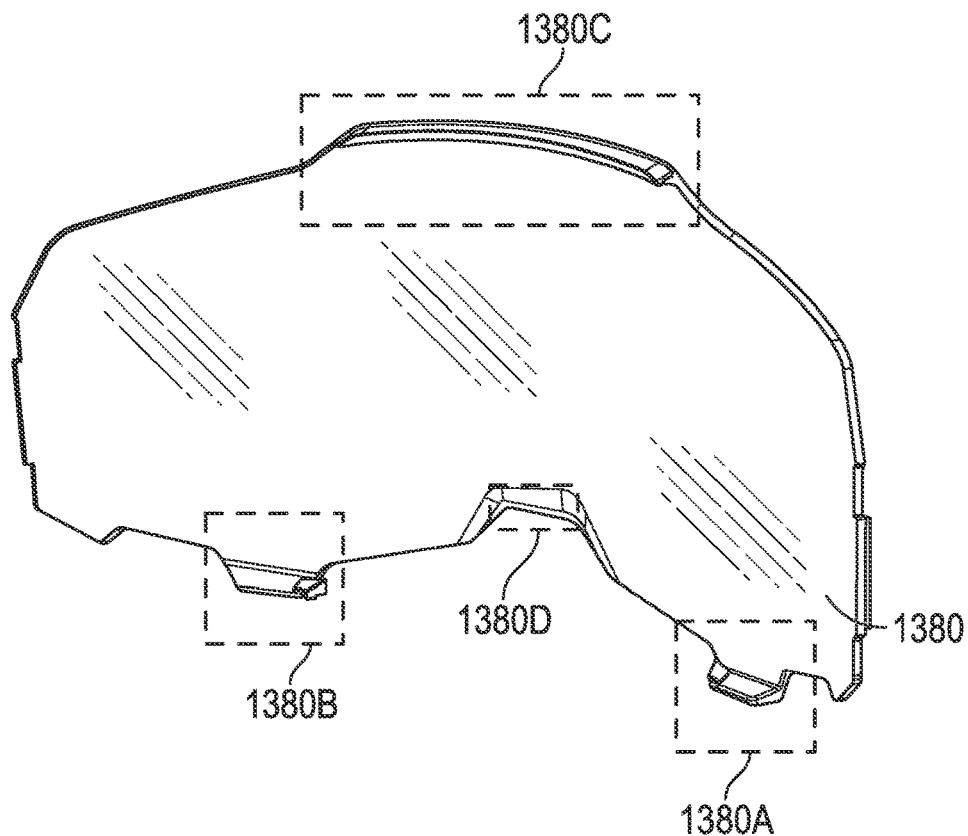
FIGS. 13A and 13B show views of another goggle lens, in accordance with an embodiment.
Figure 13B:
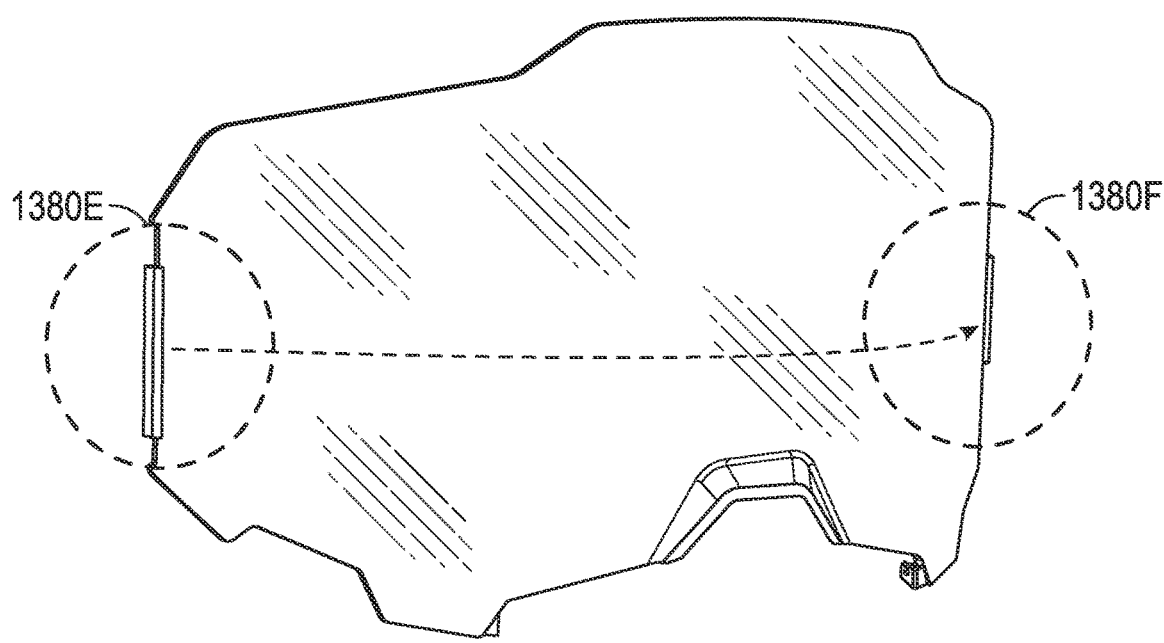

FIGS. 13A and 13B show views of another goggle lens, in accordance with an embodiment. FIGS. 13A and 13B illustrates goggle lens 1308 and protrusions 1380A-F. Protrusions 1380A-F may be oriented to allow for coupling to features of a goggle frame (e.g., goggle frame 1404 of FIG. 14). Such protrusions 1380A-F may be oriented so that, when goggle lens 1308 is properly installed within the goggle frame, goggle lens 1308 is securely held within the goggle frame.

Figure 14:
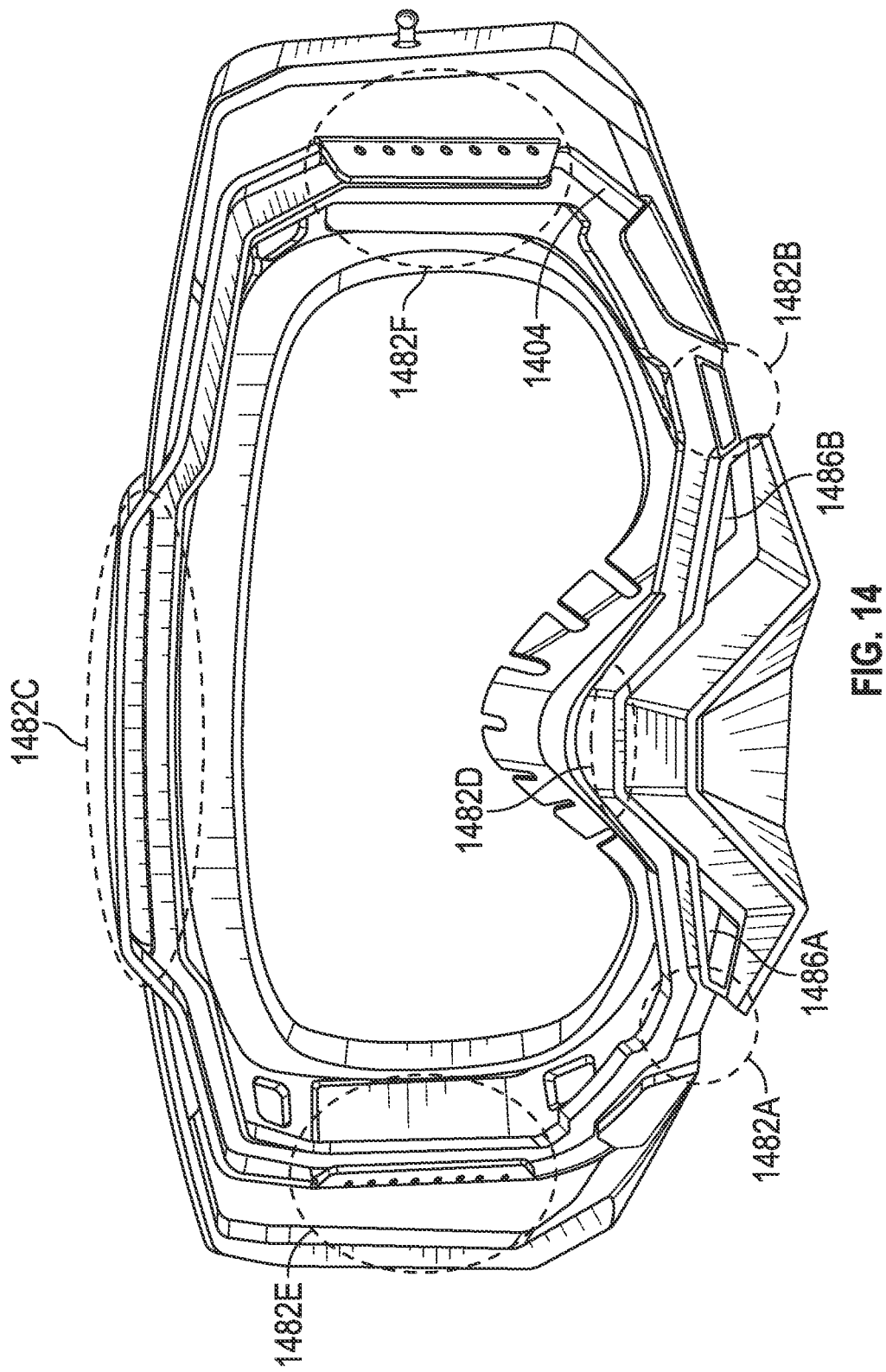
FIG. 14 shows a view of another goggle frame, in accordance with an embodiment.

For example, certain corresponding goggle frames can include engagement pockets and/or other features configured to receive protrusions 1380A-F. For example, FIG. 14 shows a view of another goggle frame, in accordance with an embodiment. Goggle frame 1404 illustrated in FIG. 14 includes features for receiving protrusions 1380A-F, such as engagement pockets shown in FIG. 14. Protrusions 1380A-C may be inward facing (e.g., facing towards the face of the wearer) and protrusions 1380D-F may be outward facing (e.g., facing away from the face of the wearer). In certain embodiments, protrusions may engage with corresponding features to securely hold goggle lens 1308 relative to goggle frame 1404.

When coupling goggle lens 1308 to goggle frame 1404, protrusions 1380A and 1380B may be inserted into engagement pockets 1482A and 1482B, respectively. Protrusions 1380A and 1380B as well as engagement pockets 1482A and 1482B may include features such as tabs and snaps that allow for engagement pockets 1482A and 1482B to securely hold goggle lens 1308 in place when goggle lens 1308 is fully coupled to goggle frame 1404. Thus, protrusions 1380A and 1380B may include snaps that, when protrusions 1380A and 1380B are fully inserted into engagement pockets 1482A and 1482, hold protrusions 1380A and 13806 within engagement pockets 1482A and 1482B.

Protrusion 1380C may be inserted into engagement pocket 1482C and protrusion 1380D may be placed on or within nose area 1482D. The goggle may further include latches 1482E and 1482F. Latches 1482E and 1482F may be configured to move between open and closed positions. In the open positions, protrusions 1380E and 1380F of goggle lens 1308 may be inserted into engagement pockets behind latches 1482E and 1482F and, after they are inserted, latches 1482E and 1482F can be moved to the closed positions to hold goggle lens 1308 in a set position relative to goggle frame 1404. Latches 1482E and 1482F, as well as goggle frame 1404, may include one or more features for locking latches 1482E and 1482F in place when latches 1482E and 1482F are in the closed position. For example, latches 1482E and 1482F may include one or more snap features and goggle lens 1404 may include complementary features, or vice versa, that, when engaged holds latches 1482E and 1482F in the closed position relative to goggle frame 1404 (e.g., in a fixed special relationship). Thus, latches 1482E and 1482F can be configured to securely hold goggle lens 1308 to goggle frame 1404 and can prevent goggles lens 1308 from being decoupled from goggle frame 1404. Goggle frame 1404 and/or goggle lens 1308 may additionally include one or more gaskets to seal areas where goggle lens 1308 contacts goggle frame 1404.

Figure 15:
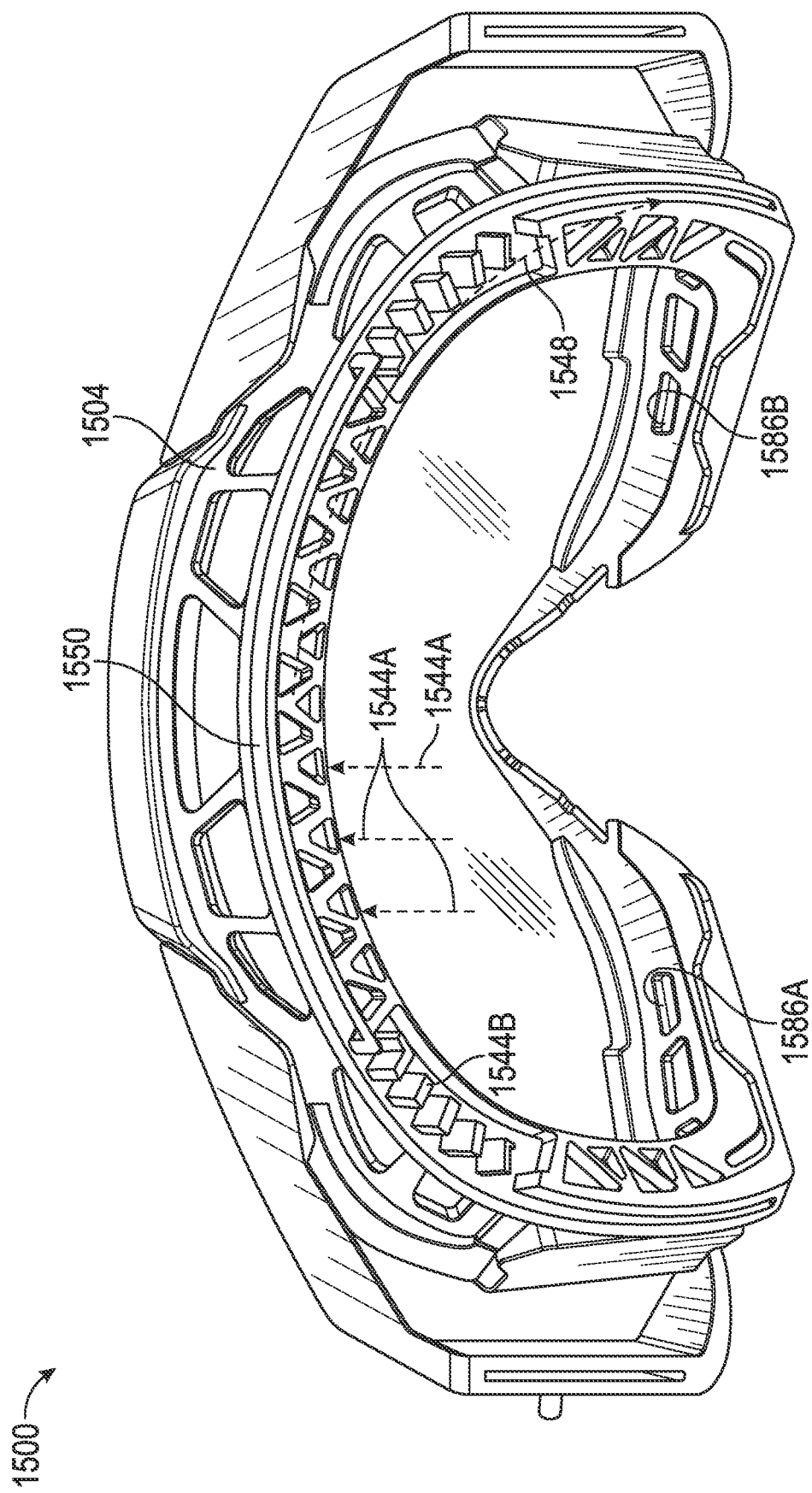
FIG. 15 shows a view of a goggle with a gutter, in accordance with an embodiment.

FIG. 15 shows a view of a goggle with a gutter, in accordance with an embodiment. Goggle 1500 includes goggle frame 1504 that includes perforations 1544A, opening 1544B, gutter 1548, and opening 1550. Gutter 1548 may an open gutter (e.g., open to the environment through, at least, opening 1550). Gutter 1548 may be configured to receive moisture (e.g., sweat of a wearer) through perforations 1544A and opening 1544B and direct the moisture away from the wearer's eyes. Such moisture can flow through gutter 1548 and/or evaporate into the environment.

Figure 16:
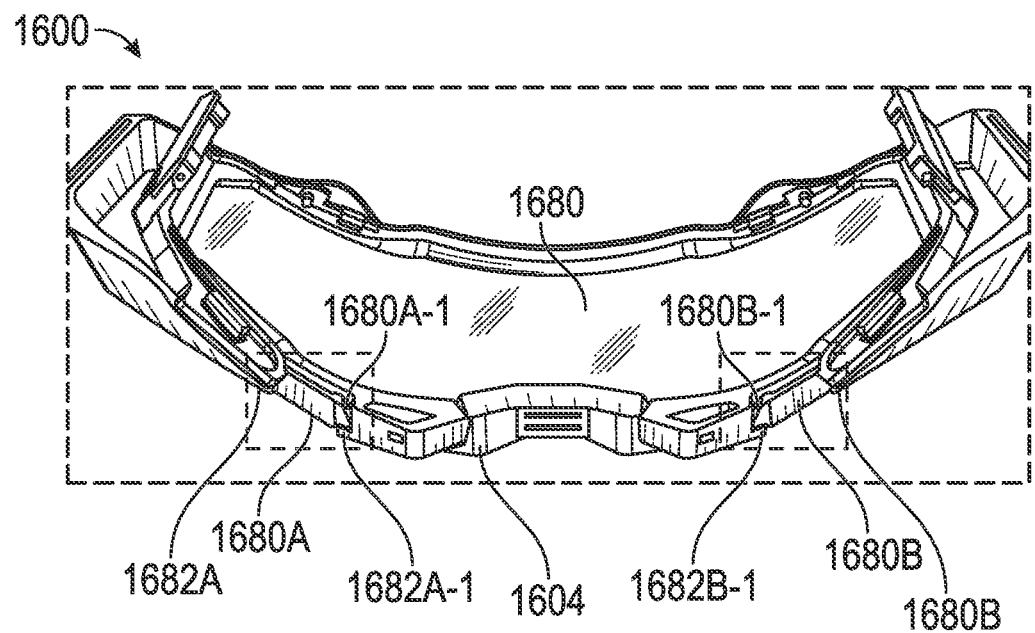
FIG. 16 shows a view of a goggle including a goggle lens and a goggle frame assembled together, in accordance with an embodiment.

FIG. 16 shows a view of a goggle including a goggle lens and a goggle frame assembled together, in accordance with an embodiment. FIG. 16 illustrates goggle 1600 that includes goggle frame 1604 and goggle lens 1608 coupled to goggle frame 1604. As shown, protrusions 1680A and 1680B may be inserted into engagement pockets 1682A and 1682B, respectively. Protrusions 1680A and 1680B may include snaps 1680A-1 and 1680B-1, respectively. Engagement pockets 1682A and 16826 include tabs 1682A-1 and 1682B-1, respectively. Engagement pockets 1682A and 1682B may be openings within the goggle frame 1604 and tabs 1682A-1 and 1682B-1 may be disposed on an end of the openings.

Snaps 1680A-1 and 1680B-1 may include a shallow angled surface configured to allow smoother insertion into engagement pockets 1682A and 1682B (e.g., by allowing for deformation of tabs 1682A-1 and 1682B-1 without requiring a large amount of force) and a steep angled surface configured to prevent decoupling of snaps 1680A-1 and 1680B-1 from engagement pockets 1682A and 1682B if a threshold amount of force is not applied to the goggle lens. The shallow angled surface may be configured to contact a portion of tabs 1682A-1 and 1682B-1 during insertion. The steep angled surface may be configured to contact a portion of tabs 1682A-1 and 1682B-1 when the goggle lens and the goggle frame are assembled. As shown in FIG. 16, when protrusions 1680A and 1680B are inserted into engagement pockets 1682A and 1682B, tabs 1682A-1 and 1682B-1 can hold snaps 1680A-1 and 1680B-1, respectively, in place.

Figure 17:
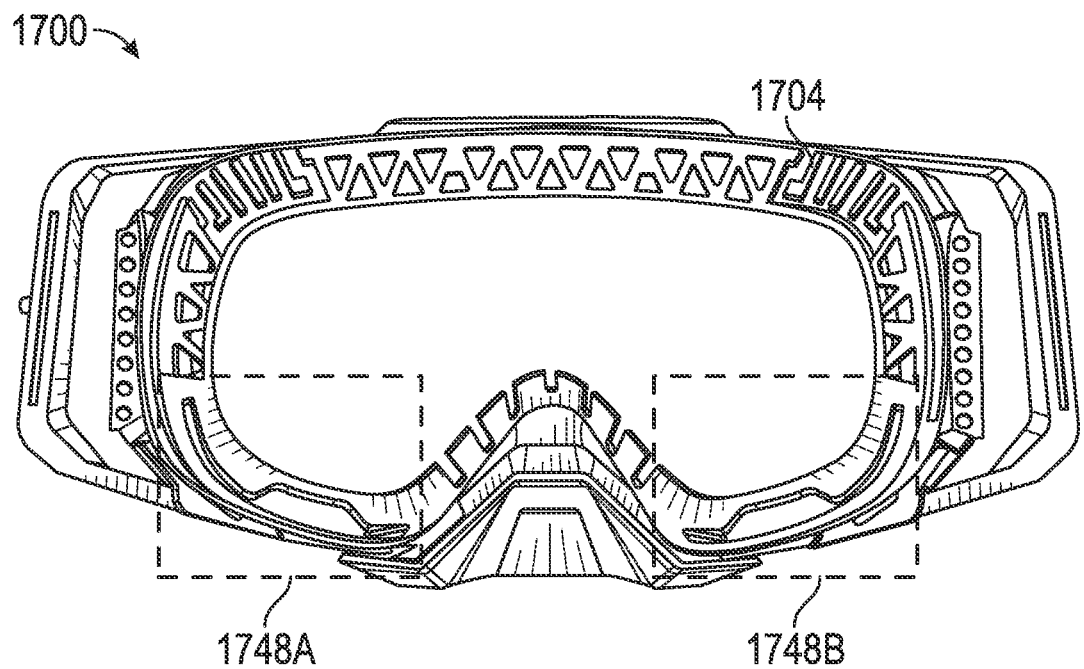
FIG. 17 shows a back view of a vented goggle frame, in accordance with an embodiment.

FIG. 17 shows a back view of a vented goggle frame, in accordance with an embodiment. FIG. 17 illustrates goggle 1700 with goggle frame 1704. Goggle frame 1704 includes air flow apertures 1748A and 1748B. Air flow apertures 1748A and 1748B may be located on the back side of goggle frame 1704, closer to the wearer's face. Intakes (e.g., intakes 1486A and 1486B, shown in FIG. 14) on the front of goggle frame 1704 can receive air flow and direct such air flow to air flow apertures 1748A and 1748B through one or more air flow channels (e.g., air flow channels 1586A and 1586B shown in FIG. 15) of goggle frame 1704. Such channels may include channels that constitute gutter 1548 or portions thereof. In certain embodiments, such channels may, in contrast to gutter 1548, be contained within goggle frame 1704 to direct all air received by intakes 1486A and 14866 through air flow apertures 1748A and 17486. Air flow apertures 1748A and 17486 may provide air flow to cool gaskets or foam padding, or portions thereof, attached to goggle frame 1704. Such air flow may flow through the gaskets or foam padding, which may be porous.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the invention may include only some of the described embodiments. Accordingly, the invention is not to be seen as limited by the foregoing description, but is only limited by the scope of the appended claims.

The invention claimed is:

1. A goggle comprising:
   a frame comprising:
   a first frame surface;
   a second frame surface;
   a connecting surface connected to the first frame surface and the second frame surface to define a gutter; and
   a gasket coupled to a first side of the second frame surface, the gasket configured to conform to a portion of a user's face and also configured to pass moisture from the user's face to the second frame surface.

2. The goggle of claim 1, wherein the second frame surface is configured to be disposed closer to the user's face than the first frame surface when the frame is worn by a user.

3. The goggle of claim 1, wherein the gutter further comprises a moisture exit allowing moisture to exit the gutter to flow away from the frame.

4. The goggle of claim 1, wherein the frame further comprises a lens vent configured to be disposed farther from the user's face than the first frame surface when the frame is worn by the user.

5. The goggle of claim 1, wherein the gasket is configured to cover an air flow aperture defined through the second frame surface, and wherein the gasket is configured to receive and pass air flow from the air flow aperture.

6. The goggle of claim 1, wherein the frame defines an interior portion and wherein the connecting surface defines at least a portion of a perimeter of the interior portion.

7. The goggle of claim 1, wherein the gutter is an open gutter.

8. A goggle comprising:
   a frame comprising:
   a first frame surface;
   a second frame surface configured to be disposed closer to a user's face than the first frame surface when the frame is worn by the user; and
   a connecting surface connected to the first frame surface and the second frame surface to define a gutter;
   an interior portion defined by the frame, the interior portion comprising a top portion, a left portion, and a right portion, and wherein the connecting surface defines at least the top portion and parts of the left portion and the right portion; and
   a gasket coupled to the second frame surface, the gasket configured to conform to a portion of the user's face and also configured to pass moisture from the user's face to the second frame surface.

9. The goggle of claim 8, wherein the gasket comprises a permeable material configured to facilitate liquid to pass through the gasket.

10. The goggle of claim 8, wherein the frame further comprises a lens vent configured to be disposed farther from the user's face than the first frame surface when the frame is worn by the user.

11. The goggle of claim 10, further comprising a moisture exit allowing moisture to exit the gutter to flow away from the frame.

12. The goggle of claim 11 wherein the gutter is an open gutter.

13. A goggle comprising:
   a frame comprising:
   a first frame portion spaced apart from a second frame portion;
   the second frame portion configured to be positioned adjacent to a user's face;
   a connecting surface connected to the first frame portion and the second frame portion to define a gutter, the gutter configured to receive moisture; and
   an interior portion defined by the frame, wherein the connecting surface defines at least a top portion and parts of a left portion and a right portion of the interior portion; and
   a gasket coupled to the second frame portion, the gasket configured to conform to a portion of the user's face and also configured to pass moisture from the user's face into the gutter.

14. The goggle of claim 13, further comprising a moisture exit configured to allow the moisture received in the gutter to exit the gutter and flow away from the frame.

15. The goggle of claim 14, wherein the frame further comprises a lens vent configured to be disposed farther from the user's face than the first frame portion when the frame is worn by the user.

16. The goggle of claim 13, further comprising:
   an air flow aperture defined through the second frame portion of the frame, wherein the airflow aperture is configured to direct air is directed through the air flow aperture to cool the gasket.

17. The goggle of claim 16, wherein the gasket is at least partially porous and covers the air flow aperture such that air passing through the air flow aperture flows through at least a portion of the gasket.

18. The goggle of claim 13, wherein the gasket comprises a water-permeable material configured to facilitate fluid flow through the gasket.

19. The goggle of claim 13, wherein the gutter is an open gutter.

* * * * *

UNITED STATES PATENT AND TRADEMARK OFFICE
CERTIFICATE OF CORRECTION

PATENT NO. : 11,998,489 B2
APPLICATION NO. : 17/818696
DATED : June 4, 2024
INVENTOR(S) : Michael D. Young, Dennis C. Tan and Ludovic Francis Boinnard Page 1 of 1

It is certified that error appears in the above-identified patent and that said Letters Patent is hereby corrected as shown below:

In the Claims

Column 14, Lines 65-67, Claim 16, the text "wherein the airflow aperture is configured to direct air is directed through the air flow aperture to cool the gasket." should read --wherein the airflow aperture is configured to direct air to cool the gasket.--.

Signed and Sealed this
Ninth Day of July, 2024

Katherine Kelly Vidal
*Director of the United States Patent and Trademark Office*